(12) United States Patent
Doshi et al.

(10) Patent No.: US 10,905,815 B2
(45) Date of Patent: Feb. 2, 2021

(54) MULTI-LUMEN INDWELLING CATHETER

(71) Applicant: CareFusion 2200, Inc., San Diego, CA (US)

(72) Inventors: Palak Doshi, Evanston, IL (US); Shayna Massi, Palatine, IL (US); John A. Krueger, Muskego, WI (US)

(73) Assignee: CAREFUSION 2200, INC., San Diego, CA (US)

( * ) Notice: Subject to any disclaimer, the term of this patent is extended or adjusted under 35 U.S.C. 154(b) by 81 days.

(21) Appl. No.: 15/335,133

(22) Filed: Oct. 26, 2016

(65) Prior Publication Data

US 2018/0110962 A1 Apr. 26, 2018

(51) Int. Cl.
*A61M 25/00* (2006.01)
*A61M 1/28* (2006.01)
*A61M 25/02* (2006.01)

(52) U.S. Cl.
CPC .......... *A61M 1/285* (2013.01); *A61M 25/003* (2013.01); *A61M 25/0017* (2013.01); *A61M 2025/0031* (2013.01); *A61M 2025/0073* (2013.01); *A61M 2025/0293* (2013.01)

(58) Field of Classification Search
CPC ............ A61M 25/003; A61M 25/0038; A61M 25/007; A61M 2025/0031; A61M 2025/0037; A61M 2025/0032
See application file for complete search history.

(56) References Cited

U.S. PATENT DOCUMENTS

| 4,995,865 A | 2/1991 | Gahara et al. |
| 5,425,723 A | 6/1995 | Wang |
| 5,738,649 A | 4/1998 | Macoviak |
| 5,797,869 A | 8/1998 | Martin et al. |

(Continued)

FOREIGN PATENT DOCUMENTS

| CN | 105358206 A | 2/2016 |
| EP | 3081238 A2 | 10/2016 |
| WO | WO-2014197614 A2 * | 12/2014 ......... B29C 67/0022 |

OTHER PUBLICATIONS

International Search Report and Written Opinion of the International Searching Authority dated Feb. 6, 2018 for PCT Application No. PCT/US2017/057362 (15 pp.).

(Continued)

*Primary Examiner* — Laura A Bouchelle
(74) *Attorney, Agent, or Firm* — Dinsmore & Shohl LLP

(57) ABSTRACT

In one aspect, the present disclosure provides a catheter, the catheter with a distal length extending to a distal end, the distal length configured to indwell a cavity of a patient body. The distal length may include a first lumen extending longitudinally through a lengthwise portion of the distal length, where the first lumen may be at least partially defined by a first inner diameter surface of the distal length. The distal length may include a second lumen extending longitudinally through the lengthwise portion of the distal length, where the second lumen may be at least partially defined by a second inner diameter surface of the distal length. A first fenestration may be disposed through a side wall of the first lumen. A proximal length of the catheter may include a proximal lengthwise portion of the first lumen and the second lumen.

15 Claims, 12 Drawing Sheets

(56) References Cited

U.S. PATENT DOCUMENTS

| | | | |
|---|---|---|---|
| 6,758,836 B2 * | 7/2004 | Zawacki | A61M 1/3653 |
| | | | 604/284 |
| 6,808,510 B1 | 10/2004 | DiFiore | |
| 7,615,034 B2 | 11/2009 | DiFiore | |
| 2003/0149395 A1 | 8/2003 | Zawacki | |
| 2003/0153898 A1 * | 8/2003 | Schon | A61M 25/0009 |
| | | | 604/544 |
| 2006/0058731 A1 | 3/2006 | Burnett et al. | |
| 2007/0073271 A1 | 3/2007 | Brucker et al. | |
| 2007/0255230 A1 * | 11/2007 | Gross | A61B 17/8811 |
| | | | 604/272 |
| 2008/0097562 A1 * | 4/2008 | Tan | A61M 5/44 |
| | | | 607/105 |
| 2009/0292248 A1 * | 11/2009 | Schon | A61M 25/0026 |
| | | | 604/164.01 |
| 2016/0114124 A1 * | 4/2016 | Tal | A61M 25/0029 |
| | | | 604/43 |

OTHER PUBLICATIONS

International Preliminary Report on Patentability dated May 9, 2019 pertaining to International Application No. PCT/US2017/057362.
Chinese Office Action dated Jan. 14, 2020 with reference to related Chinese Application No. 201711013015.1.
Examination Report dated Jun. 17, 2020 pertaining to European Patent Application No. 17794502.9.
Office Action dated Jul. 15, 2020 pertaining to Chinese Patent Application No. 201711013015.1.

* cited by examiner

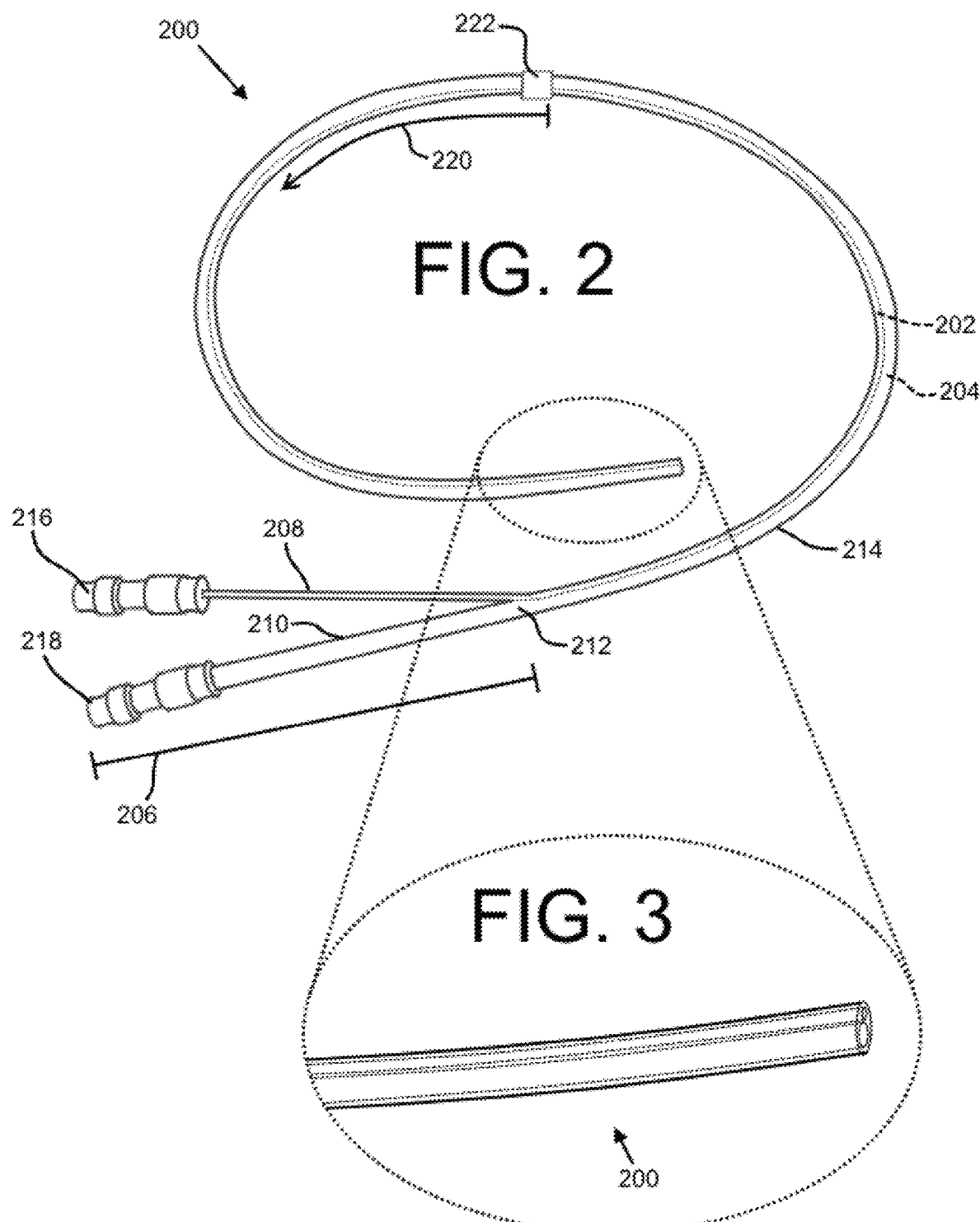

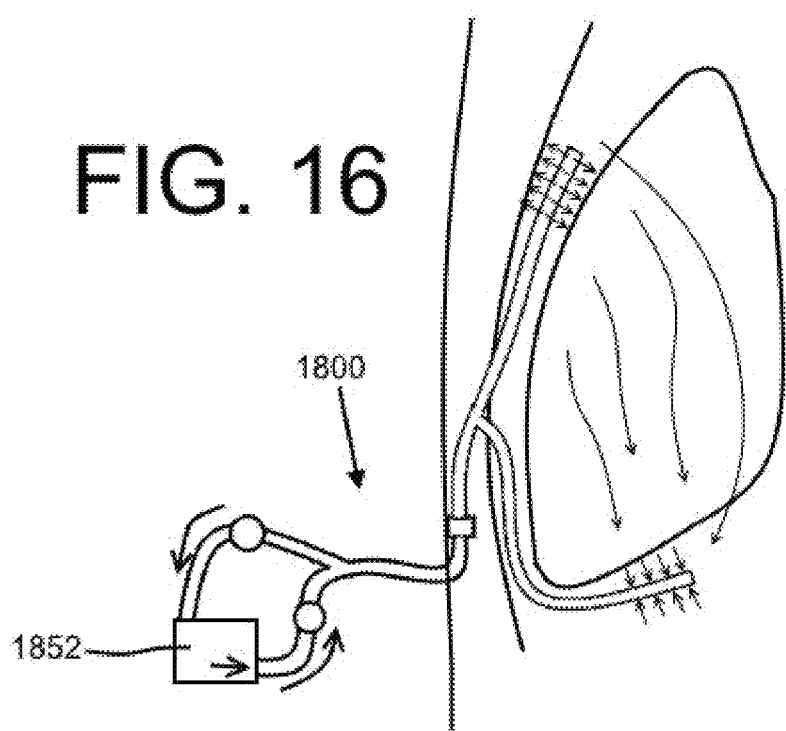

MULTI-LUMEN INDWELLING CATHETER

TECHNICAL FIELD

Embodiments of the present disclosure relate to methods and devices for performing medical procedure involving a drainage function and/or an injection function.

BACKGROUND

Chemotherapy generally refers to the use of medicines or drugs to destroy cancer cells. Typically, the chemotherapy drugs are delivered via intravenous methods or by taking capsules orally, thereby distributing the drug throughout the body. The toxic nature of the drug often affects healthy cells as well as cancer cells, which can cause a series of unpleasant side effects such as nausea, damage to the immune system, fatigue, and hair loss.

Recently, it has been found that cancer cells may be treated with localized application of chemotherapy drugs. For example, in one procedure called heated intraperitoneal chemoperfusion ("HIPEC"), warmed chemotherapy medication is circulated in the peritoneal cavity immediately after the surgical removal of tumors. The chemotherapy drugs are then removed from the peritoneal cavity after a short time to prevent substantial damage to surrounding body tissue. While effective, HIPEC can only be performed after invasive surgical procedures granting sufficient access to the body cavity. Because surgical procedures are typically infrequent, repeat local application is usually not possible since access to the body cavity is generally limited in duration.

In view of this background, a medical device providing access to a body cavity for the injection and drainage of a medication without substantial invasiveness would be advantageous.

BRIEF SUMMARY

In one aspect, the present disclosure provides a catheter, the catheter with a distal length extending to a distal end, the distal length configured to indwell a cavity of a patient body. The distal length may include a first lumen extending longitudinally through a lengthwise portion of the distal length, where the first lumen may be at least partially defined by a first inner diameter surface of the distal length. The distal length may include a second lumen extending longitudinally through the lengthwise portion of the distal length, where the second lumen may be at least partially defined by a second inner diameter surface of the distal length. A first fenestration may be disposed through a side wall of the first lumen, where the first fenestration may be configured to form an outlet of the first lumen. A proximal length of the catheter may include a proximal lengthwise portion of the first lumen and a proximal lengthwise portion of the second lumen. A cuff element may be disposed on an outer surface of the proximal length.

The proximal length may include a bifurcated length having a first tube portion and a second tube portion, where the first lumen extends longitudinally through the tube first portion, and where the second lumen extends longitudinally through the second tube portion.

The first tube portion may include a first valve configured for an injection procedure, and the second tube portion may include a second valve configured for a drainage procedure.

A distal end of the distal length may include the first lumen with a plurality of fenestrations spaced longitudinally, where the space between the fenestrations decreases closer to a distal terminus.

A distal end of the distal length may include the first lumen with a plurality of fenestrations spaced longitudinally, where a cross-sectional size of the fenestrations increases closer to a distal terminus.

The distal length may include a distal bifurcated length having a first distal tube portion and a second distal tube portion, where the first lumen extends through the first distal tube portion and the second lumen extends through the second distal tube portion.

A diameter of the second lumen may be at least two (2) times as large as a diameter of the first lumen.

The proximal length may include a first proximal tube portion with an injection port.

BRIEF DESCRIPTION OF THE DRAWINGS

FIG. 2 shows an embodiment of a dual lumen indwelling catheter in accordance with the present disclosure.

FIG. 3 shows a magnified view of the distal end of the dual lumen indwelling catheter of FIG. 2.

FIG. 16 shows an embodiment of a dual lumen indwelling catheter with a circulating pump in accordance with the present disclosure.

DETAILED DESCRIPTION

Figure 1:
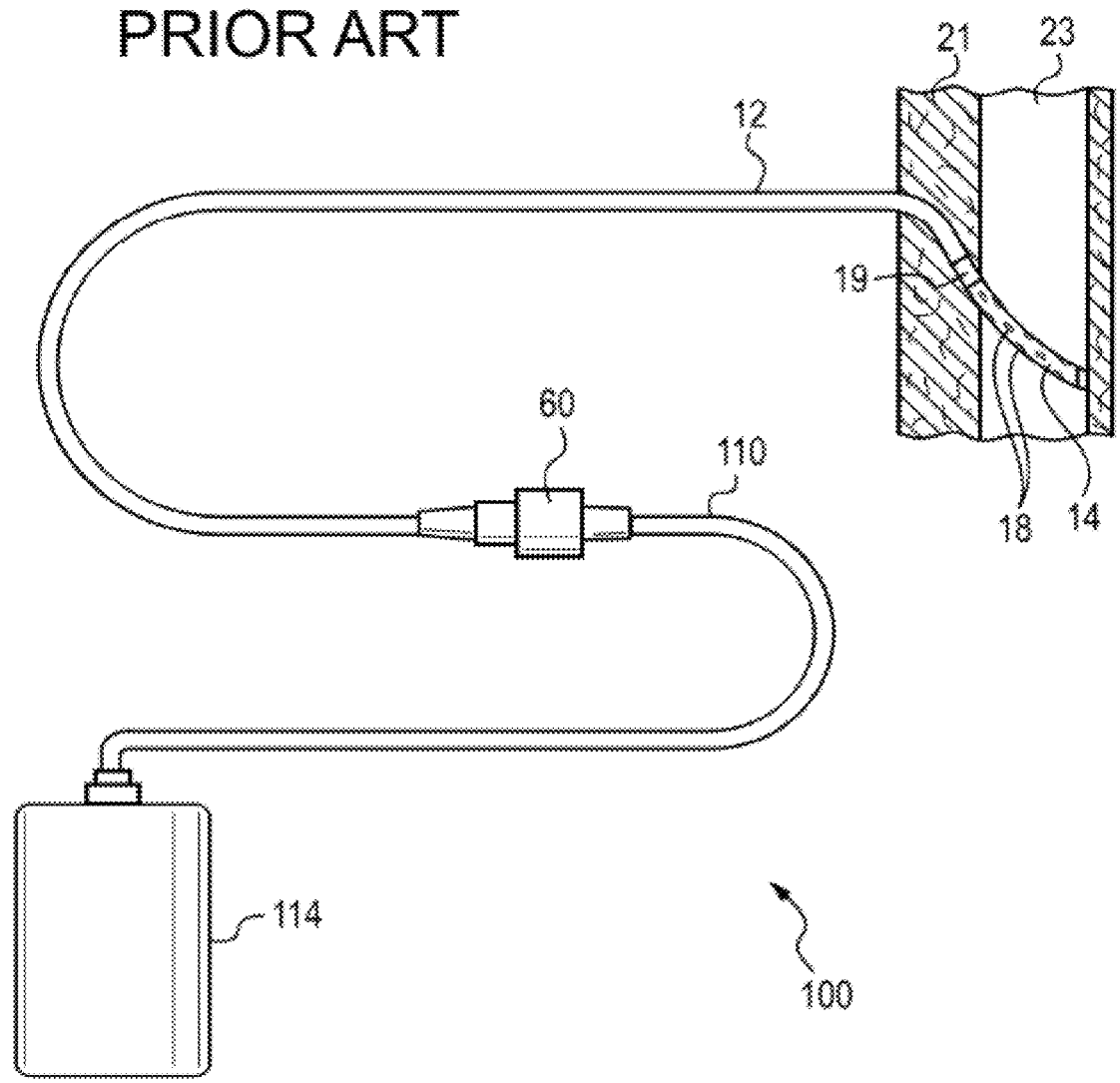
FIG. 1 illustrates a drainage apparatus as known in the prior art.

Embodiments generally are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale (including that relative lengths and other proportions may be the same as or different than various illustrations herein), and in certain instances details may have been omitted that are not necessary for an understanding of embodiments of the present invention, such as—for example—conventional fabrication and assembly.

Medical drainage procedures may be performed with drainage devices of the type shown in FIG. 1. The apparatus 100 is shown as installed in a patient body and includes a drainage container 114. The drainage container 114 is removably attached by a proximal tube 110 at a valve 60 to a distal catheter 12. The valve 60 may be configured in any number of ways known in the art for attaching catheters together in a fluid-patent manner, (which may include a two-part valve), and the proximal portion attached to the distal catheter 12 may be configured to be self-sealing when disconnected from the proximal tube 110. The proximal end portion of the distal catheter 12 is shown indwelling the patient, disposed through the body wall 21 into an intra-body space 23, which may be—for example—a pleural, peritoneal, or other body lumen. That proximal portion includes a cuff element 19 and a flexible fluid-intake length 14 including fenestrations 18, shown in the intra-body space 23. This structure may be better understood with reference to U.S. Pat. No. 5,484,401, which is herein incorporated by reference in its entirety, and with reference to commercial products marketed under the name PleurX® by CareFusion® of San Diego, Calif. Another structure that may be useful for providing such a method is disclosed in U.S. App. Pub. No. 2015/0174375 to DeVries et al., which is herein incorporated by reference in its entirety and with reference to commercial products marketed under the name PleurX® by CareFusion® of San Diego, Calif.

It would additionally be advantageous to provide a single indwelling catheter that can perform the above-described drainage function, but also can deliver a drug to a body cavity without substantially increasing the invasiveness of the device. FIG. 2 shows an embodiment of a dual lumen indwelling catheter, depicted as the catheter 200, which may be configured to indwell a body trunk cavity that provides one or both of a drainage function and an injection function, including seriatim or simultaneously. The catheter 200 may be a silicone multi-lumen catheter for long term pleural access to administer medication and drain fluid (i.e., drug and effusion). The catheter 200 may allow for a patient to perform drainage and drug administration at home and/or allow for multiple treatments over time with minimal inconvenience to the patient. This device can be used to, among other things, deliver therapy for malignant or benign conditions including pulmonary fibrosis and malignant mesothelioma, and cancers with lung metastases.

The catheter 200 is depicted with two lumens: a first lumen 202 and a second lumen 204. The first lumen 202 and the second lumen 204 may extend longitudinally through at least a lengthwise portion of a bifurcated length 206 and a binal portion 214. The first lumen 202 and the second lumen 204 may be configured for particular functions. For example, the first lumen 202 may be configured primarily for the delivery of a substance (e.g., a medication for effecting pleurodesis or a medication for treating cancer) to a target area within the body of a patient, while the second lumen 204 may be configured primarily for a drainage procedure. While not shown, it is contemplated that more than two lumens may be included. The two lumens (in a binal embodiment) most preferably are parallel for their entire respective lengths and are not coaxial along any lengthwise portion, although one or both may have a non-circular cross-section and partially surround the other. However, one preferred embodiment includes two lumens along the binal portion that each have a circular cross-section, and that are parallel to each other and a longitudinal central axis of the binal portion.

The proximal end of the catheter 200 may include the bifurcated length 206 with a first tube portion 208 and a second tube portion 210. The first lumen 202 may extend through the first tube portion 208 and the second lumen 204 may extend through the second tube portion 210, as shown. In at least one exemplary embodiment, the first tube portion 208 and the second tube portion 210 may be about 4 inches in length (but any suitable length may be used). The length of the first tube portion 208 and the second tube portion 210 may be substantially the same or different. The first tube portion 208 and the second tube portion 210 may join at a junction 212. The binal portion 214, which may be made of a flexible silicone providing patient comfort, may extend distally from the junction 212, and may include the two lumens 202, 204 extending longitudinally therethrough. The binal portion 214 may be a flexible tube-like structure with two inner diameter surfaces substantially defining side walls of at least a portion of the two lumens 202, 204. The binal portion 214 of the catheter 200 may have any suitable length (such as approximately 16 inches in at least one exemplary embodiment). A distal length 220 of the binal portion 214 may be configured to be placed in the body of a patient temporarily or permanently (for example, for a time period of about 6-8 weeks in a non-limiting exemplary embodiment). Herein, the distal length 220 may be the length of the binal portion 214 that is designed for entry into a patient body, while a so-called proximal length may be the length of the catheter 200 (including both a length of the binal portion 214 and the bifurcated length 206) that generally remains external to the patient body.

The first tube portion 208 and/or the second tube portion 210 may be associated with a valve (or port) 216, 218. It is contemplated that the valves 216, 218 may be configured for the particular function of their associated lumens. For example, the first tube portion 208 may include the first valve 216 which may be configured for the delivery of a medication or another substance. Exemplary valves include Texium® and Smartsite® valves marketed by CareFusion® of San Diego, Calif. The first valve 216 may be associated with a suitable injection system, such as—for example—a syringe, a pressurized injector, a pump, or any other appropriate means for injection. It is contemplated that the first valve 216 may be designed to be operable (i.e., openable) only by a medical professional and/or only with corresponding equipment generally available only at a medical facility, which may prevent inadvertent and improper access by a patient.

The second tube portion 210 may include a second valve 218, which may be configured for a drainage procedure. An exemplary second valve 218 may be a valve marketed under the name PleurX® by CareFusion®, and may be designed for use with drainage equipment, such as vacuum bottles and other suction devices, drainage bags, or the like. It is contemplated that the second valve 218 may be operable by the patient without the presence of a medical professional. Advantageously, the described embodiment of the catheter 200 having the first valve 216 and the second valve 218 may simultaneously provide the ability for (1) a medical professional to inject a medication into a patient as needed with a first lumen 202 without risk of the patient inadvertently or improperly accessing the first lumen 202 and (2) the patient to access the second lumen 204 for drainage purposes without the presence of the medical professional. The valves 216, 218 and/or the tube portions 208, 210 may be individually marked for ease of identification.

A cuff element 222 may be located at the proximal end of the distal length 220. The cuff element 222 may be provided on the outer surface of the binal portion 214. When installed, at least the outer diameter surface of the cuff element 222 may contact the skin or other tissue (such as the tissue surface of an incision) at or near the location where the catheter 200 enters the body. In some embodiments, for example, the cuff element 222 may be tunneled into the body about 1 cm past the incision, and it is contemplated that the cuff element 222 may not be exposed outside the body. The cuff element 222 may be textured or otherwise configured to allow and facilitate tissue ingrowth. Over time, the skin or other tissue of the patient may become secured to the cuff element 222, and the cuff element 222 may provide a seal between internal and external of the patient's body, thereby reducing the risk of infection and other medical complications. In other words, the cuff element 222 may become part of a sealed barrier continuous and contiguous with the rest of the patient's skin as an integrated part of his/her natural epidermal barrier. The cuff element 222 may be made of Dacron™ or another suitable material. The cuff element 222 may incorporate an adhesive or another suitable means for attachment/sealing to be used in combination with, or as an alternative to, tissue ingrowth. It is contemplated that a location immediately adjacent the cuff may include a micro-textured surface that may inhibit microbial colonization and migration in/toward the patient's body as described in U.S. patent application Ser. No. 15/169,410 to Krueger et al., which is herein incorporated by reference in its entirety.

The binal portion 214 may be formed of a flexible and biocompatible material suitable for deployment in a body trunk cavity. In some embodiments, the binal portion 214 may include a memory-material configured to guide at least the distal end of the catheter 200 to a target location in a patient body. The memory material may include any appropriate metallic or polymeric material upon which shape-memory may be imposed, while allowing flexibility. For example, various nitinol and other memory metal compounds are well-known and commonly used in the medical device art. Other materials can receive and default-return to a shape (imposed by mechanical, temperature, and/or other means) after flexure into different shape(s). The memory configuration may be assumed based upon temperature, release of constraint, and/or by active means. The binal portion 214 may additionally or alternatively include one or more one visualization markers 215 configured to be visualizable in a patient body by at least one of fluoroscopy, ultrasound, magnetic resonance imaging, and computed tomography, or another suitable technology. The visualization marker(s) may assist medical personnel during deployment of the catheter 200, for example.

The lumens 202, 204 may have any suitable cross-sectional size. For example, when the lumens 202, 204 have circular cross-sections (see FIG. 3), the diameter of the lumens 202, 204 may be between about 0.005 inches and about 1 inch, such as from about 0.030 to about 0.300 inches. As best shown by FIG. 3, the first lumen 202 and the second lumen 204 may have different cross-sectional dimensions. For example, the diameter of the first lumen 202 may be a diameter suitable for a relatively precise injection procedure (such as a diameter of about 0.050 inches), and the diameter of the second lumen 204 may be suitable for the performance of a relatively less-precise drainage procedure (such as about 0.100 inches). The diameter (or other cross-sectional dimension) of the second lumen 204 may be about 1.5 times larger than the diameter (or other cross-sectional dimension) of the first lumen 202, about 2 times larger, about 3 times larger, about 4 times larger, etc. In one exemplary embodiment, the diameter of the first lumen 202 may be about 0.044 inches (and the outer diameter of the tube forming the first lumen 202 may be about 0.063 inches), and the diameter of the second lumen 204 may be about 0.095 inches (and the outer diameter of the tube forming the second lumen 204 may be about 0.200 inches), which may provide a desirable flow rate and wall thickness in certain medical applications.

Figure 4:
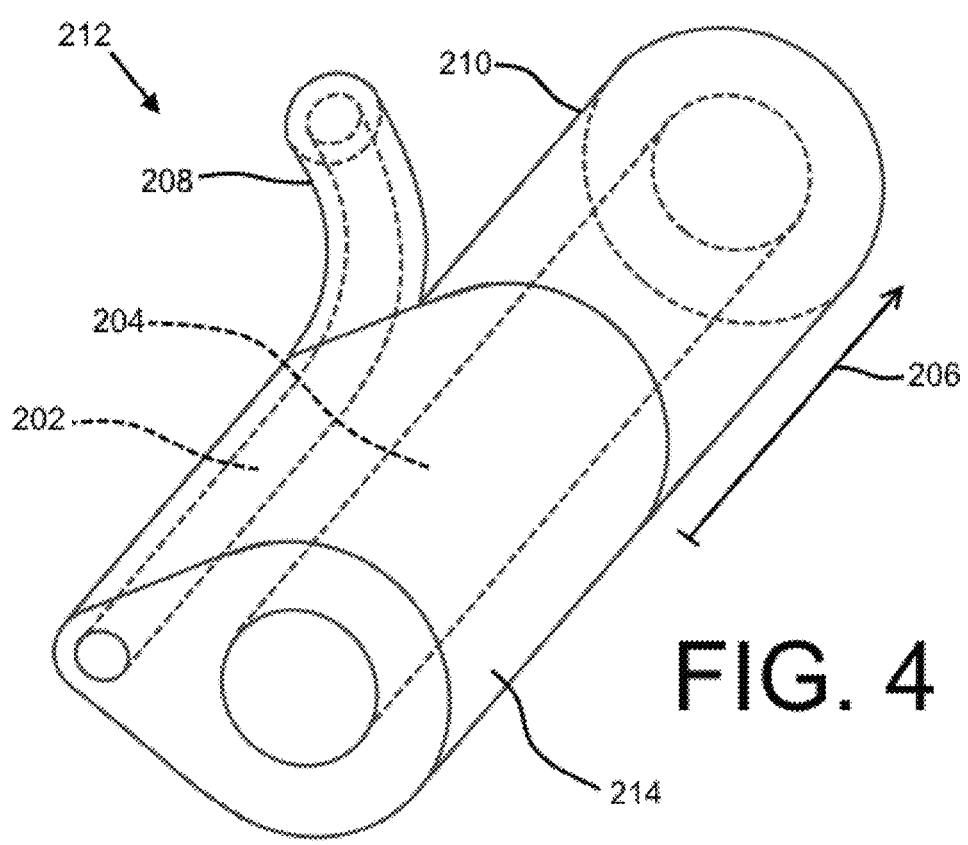
FIG. 4 shows an embodiment of a junction for a dual lumen indwelling catheter in accordance with the present disclosure.

FIG. 4 shows an embodiment of the junction 212 in detail. The junction 212 may be a separate component from tubing forming the bifurcated length 206 and/or the binal portion 214 (e.g., it may be a component formed separately from, and then attached to, the first tube portion 208, the second proximal tube 210, and/or the binal portion 214). In some embodiments, the binal portion 214 may merely be a point where two tubes are connected to one another at a contact point (through use of an adhesive, through fusing, etc.) (see FIG. 2). The junction 212 and/or the binal portion 214 may be ovular in cross-section, as shown, but this is not required. However, it may be advantageous to use an ovular cross-section when two lumens 202, 204 are provided due to the relatively small surface area and relatively smooth and continuous outer-perimeter shape. While not shown, the junction may include a visual indicator, such as a barium stripe.

Figure 5:
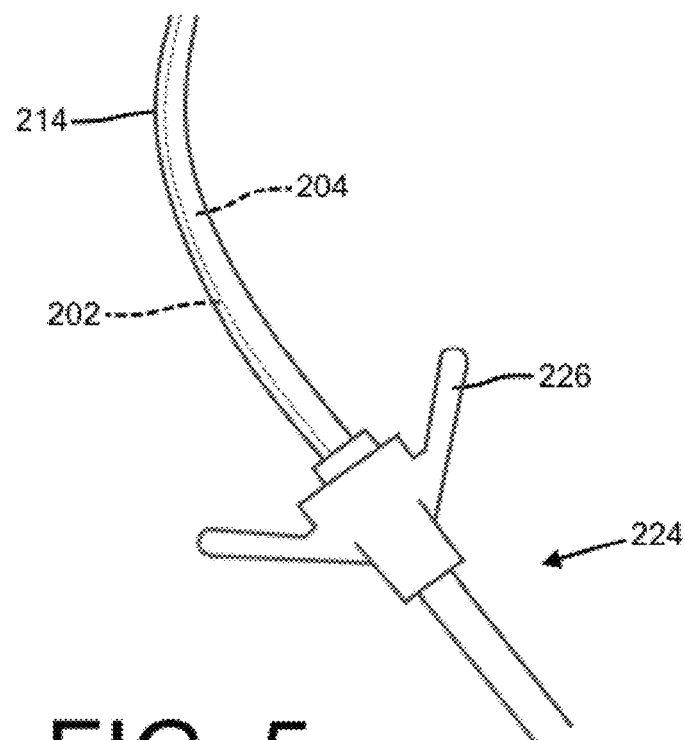
FIG. 5 shows a system with a dual lumen indwelling catheter and an introducer in accordance with the present disclosure.

Referring to FIG. 5, in some embodiments, the binal portion 214 may be sized or otherwise configured to be directed through an introducer 224, which may include a pinch valve 226 as shown. For example, the outer perimeter of the binal portion 214 may be configured (e.g., dimensioned) to fit within a channel of a commercially-available introducer 224. Advantageously, the valved introducer 224 may control both lumens 202, 204 at the same time, which may be desirable when a medical function requires synchronized function of the lumens 202, 204, for example. The introducer 224 may be configured as a commercially available splittable introducer of any type already known in the art for introduction of a tubular device through a body wall or other structure, followed by subsequent removal of the introducer circumferentially encompassing the introduced device.

Figure 6:
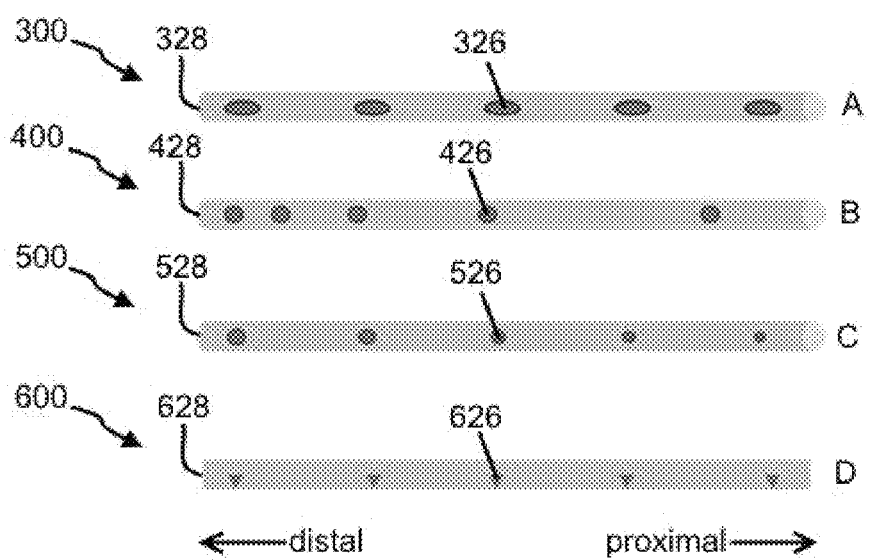
FIG. 6 shows a bottom view of four (4) embodiments of a distal end of a dual lumen indwelling catheter with fenestrations in accordance with the present disclosure.

FIG. 6 shows a bottom view of four embodiments of a distal end of a dual lumen indwelling catheter 300 with fenestrations 326 through the side wall of at least one lumen. The fenestrations 326 may serve as an inlet and/or an outlet for one or more lumens of the catheter 300, such as an injection lumen (e.g., the first lumen 202 of FIG. 1-FIG. 2) and/or a drainage lumen (e.g., the second lumen 204 of FIG. 1-FIG. 2). In some embodiments, the fenestrations 326 may serve as the only inlet or outlet, but in other embodiments an opening may be provided at the distal terminus 328 of the catheter 300 (as shown in FIG. 2, for example). As shown in embodiment A of FIG. 6, the fenestrations 326 may be spaced apart with approximate consistency along the length of the distal end of the catheter 300. Also, as depicted, the fenestrations 326 may be elliptical rather than circular in cross-section, though no particular shape is required in the present disclosure. Each of the fenestrations may be about the same size, as shown. The fenestrations may also have valve-type configuration(s) that render them effectively one-way for inlet or outlet functionality.

A catheter 400 may have fenestrations 426 with an unequal spacing, as depicted by embodiment B. For example, as shown, the space between each of the fenestrations 426 may decrease nearer a distal terminus 428.

Advantageously, this embodiment may provide a relatively even distribution of medication when the fenestrations 426 are associated with an injection lumen. The advantageous characteristics of this embodiment are discussed in more detail with respect to FIG. 7 below.

Referring to embodiment C, the size of two or more fenestrations 526 may vary along the length of a catheter 500. For example and as shown, the size of the fenestrations 526 may increase nearer a distal terminus 528. Similar as to in embodiment B, this embodiment may provide a relatively even distribution of medication when the fenestrations 526 are associated with an injection lumen, which is described in more detail below with respect to FIG. 7.

As represented by embodiment D of FIG. 6, a catheter 600 may have fenestrations 626 with a cross-sectional shape that acts as a nozzle.

Advantageously, the nozzle-like fenestrations 626 may inject a medication or other substance into the body of a patient with a relatively high velocity and may focus the flow of the medication precisely on a target location within the patient body. The nozzle-like fenestrations 626 may be any suitable shape and size. Further, two or more of the shape, size, and spacing characteristics described herein can be combined in any suitable manner to optimize the catheter 600 for a particular function.

Figure 7:
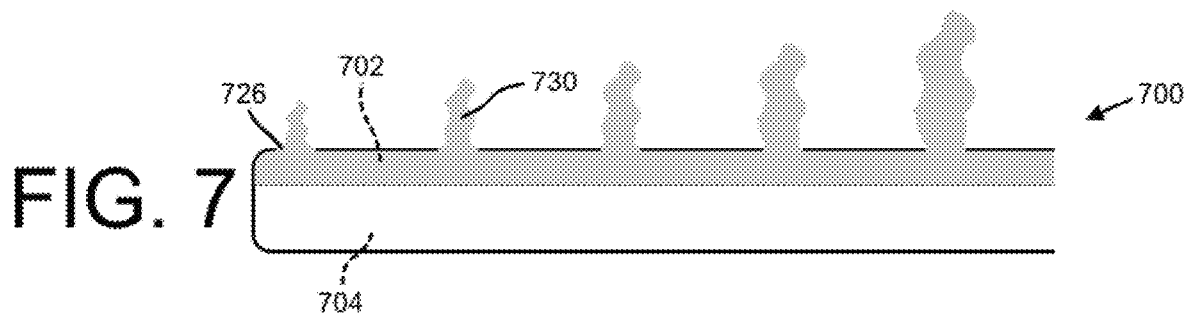
FIG. 7 shows an illustration of the flow of a substance as it is injected by a lumen of a dual lumen indwelling catheter in accordance with the present disclosure.

FIG. 7 shows an illustration of the flow of a medication (e.g., a medicament or other substance) as it is injected into the body of a patient by a first lumen 702 of a catheter 700. Medications dispensable through the first lumen 702 may include sclerosis-inducing agent(s), therapeutic agent(s), chemotherapy agent(s), gene therapy agent(s), and/or other materials. Medications may be configured as liquids, solutions, suspensions, gels, pastes, or any combination thereof and may include effervescent material (e.g., sodium bicarbonate and citric acid or other combination that can be activated by temperature, liquid-contact, or other means) configured to aid dispersion through the body cavity by formation of bubbles and/or spreading by similar means. Examples of medications may include talc, silver nitrate, bleomycin, and/or other sclerosis-inducing agents. In addition or in the alternative, examples of medicaments may include chemotherapy agents, antibiotic(s), loculation-breakup compound(s) (e.g., tissue plasminogen activator tPA), and/or other materials. A biologic fluid (e.g., a patient's own blood, immunotherapy, or other biologic agent) may be effective to provide or enhance therapeutic treatment of a pleural effusion or other condition being treated with a method and/or apparatus of the present disclosure, and may therefore be considered as a medication herein.

The catheter 700 may include the first lumen 702 with the fenestrations 726 and a second lumen 704 (which may also include fenestrations that are not shown). Each of the fenestrations 726 may be about the same size, and the spacing between each of the fenestrations 726 may be about the same. As shown, due to the physics of fluid flow as the fluid 730 moves distally through the lumen 702, the fluid 730 may experience a total pressure loss due to (1) a friction-related pressure drop and (2) a loss of pressure corresponding to a flow-rate out of the lumen 702 at each outlet (i.e., each fenestration 726). Accordingly, the injection pressure (herein defined as the pressure of the fluid 730 in the lumen 702 just before it discharges from a fenestration 726) of the fluid 730 will decrease with respect to each distally-successive fenestration 726. As a result, the fluid may be injected into a patient at a decreasing flow rate with respect to each distally-successive fenestration 726. This embodiment may be advantageous where it is desired to vary the flow rate of a medication at different locations within a patient body.

Figure 8:
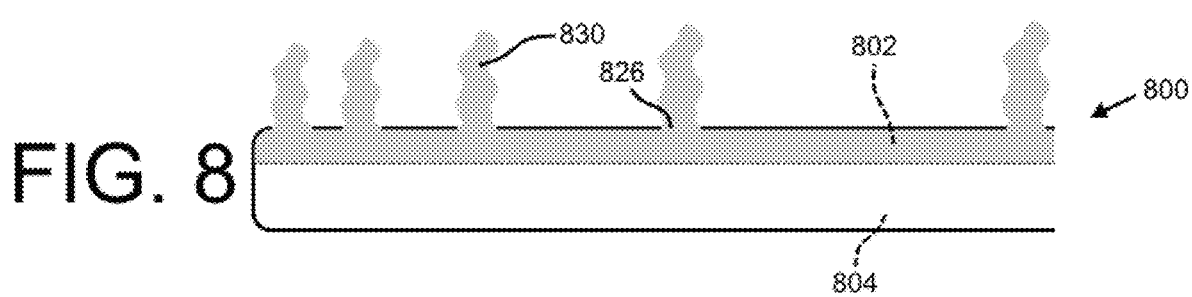
FIG. 8 shows an illustration of the flow of a substance as it is injected by a lumen of a second embodiment of a dual lumen indwelling catheter in accordance with the present disclosure.

FIG. 8 shows an illustration of an injection procedure by a second embodiment of a catheter 800 with first and second lumens 802, 804. The catheter 800 is depicted as having features similar to the catheter 700 of FIG. 7, but with decreasing spacing between the fenestrations 826 with respect to the distal direction. In this embodiment, the injection pressure of the medication 830 may be more consistent along the length of the catheter 800 such that the medication 830 is released relatively evenly (i.e., the flow rate out of each of the fenestrations 826 varies less). Advantageously, this embodiment may provide for a more consistent application of the medication at a treatment site within a patient body.

Figure 9:
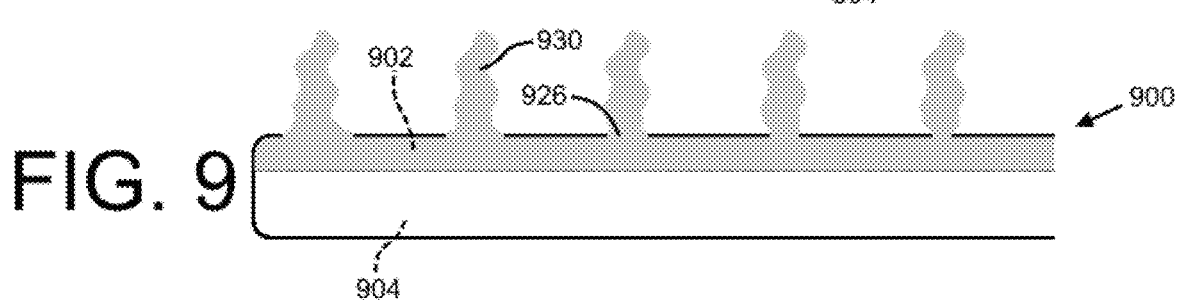
FIG. 9 shows an illustration of the flow of a substance as it is injected by a lumen of a third embodiment of a dual lumen indwelling catheter in accordance with the present disclosure.

FIG. 9 shows a similar effect may be achieved by increasing the size of each distally-successive fenestration of a catheter (for example, as shown by embodiment C of FIG. 6). A catheter 900 (with lumens 902, 904) may include fenestrations 926 that increase in size distally. In this embodiment, while the injection pressure will decrease a relatively high amount with respect to distally-successive fenestrations when compared to the embodiment of FIG. 8, the flow rate of the medication 930 out of a fenestration is a function of both (1) the injection pressure, and (2) the size (and shape) of the fenestration. Accordingly, larger fenestrations will provide for a higher injection flow rate. The size of each of the fenestrations can be optimized such that the flow rate is relatively consistent along the length of the catheter to thereby advantageously provide even distribution of the medication at a treatment site. It is contemplated that the fenestrations 926 may be designed to purposely vary the injection flow rate along the length of the catheter to vary the distribution of the medication in a controlled manner.

While the characteristics related to variations in size and spacing and shape are illustrated in isolation, a catheter may have fenestrations with a combination of varying size and varying spacing to achieve a desirable distribution of an injected medication. In addition, more than one lumen of the catheter may incorporate these described characteristics related to fenestrations. For example, referring to the catheter 200 of FIG. 2, one or both of the first lumen 202 and the second lumen 204 may incorporate fenestrations having different sizes and different spaces therebetween.

Figure 10:
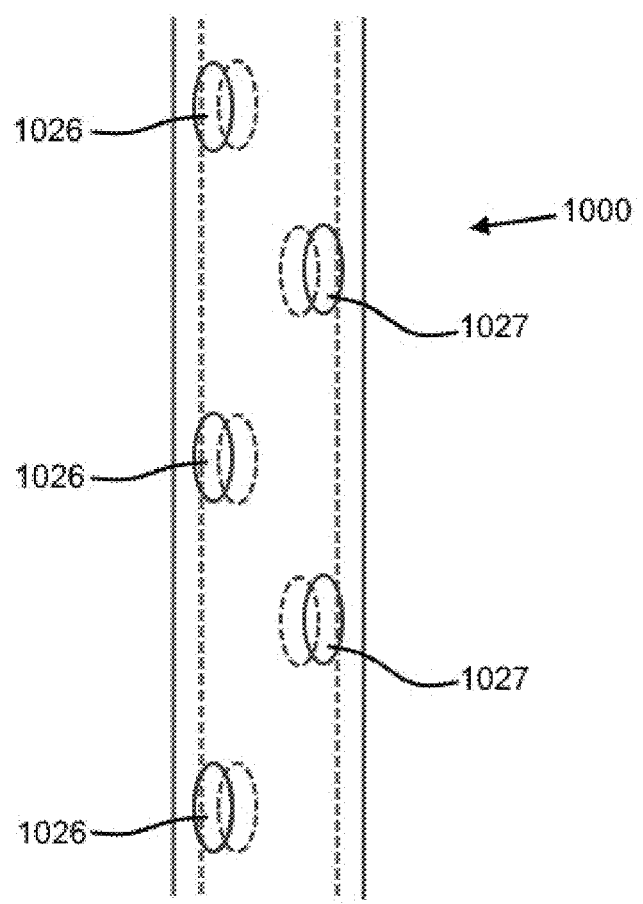
FIG. 10 shows an embodiment of a distal end of a dual lumen catheter with offset fenestrations in accordance with the present disclosure.

Further, as depicted by the embodiment of FIG. 10, a catheter 1000 may include fenestrations 1026, 1027 that are offset with respect to the longitudinal direction of the catheter 1000. This feature may be combined with any of the other fenestration-related characteristics described above. Advantageously, a medication may be injected consistently with respect to the radial direction to further enhance the distribution of a medication. While advantages of the herein-described fenestration-related characteristics are primarily described with reference to injecting a substance, those same advantages (or similar advantages) may also apply with respect to a drainage procedure.

Figure 11:
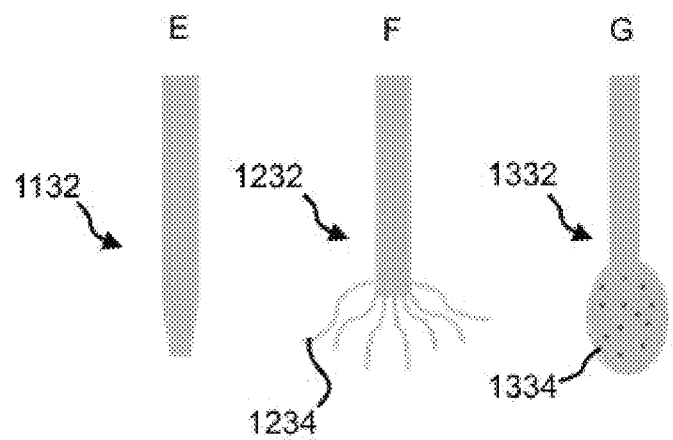
FIG. 11 shows embodiments of tips of a dual lumen indwelling catheter in accordance with the present disclosure.

In addition to, or as an alternative to, the fenestrations described above, one or more lumens of a catheter may include a distal end configured for a particular distribution of an injected medication (and/or drainage). Referring to embodiment E of FIG. 11, the distal end 1132 may include a tapered tip configured to act as a nozzle to inject a medication or other substance with a high velocity and high focus in the longitudinal direction. As shown by embodiment B, the distal end 1232 may include a plurality of extremities 1234, where each of the extremities 1234 includes at least one outlet such that the medication is injected in many different directions. It is contemplated that the extremities 1234 may be flexible, and they may be protected by a removable sheath (not shown) during the deployment of the catheter, for example. A balloon tip 1334 with a plurality of outlets may be included on the distal end 1332 as shown by embodiment C. The balloon tip 1334 may be in fluid communication with at least one lumen of the catheter, and may expand when under pressure (e.g., when an injection pressure is present).

Figure 12:
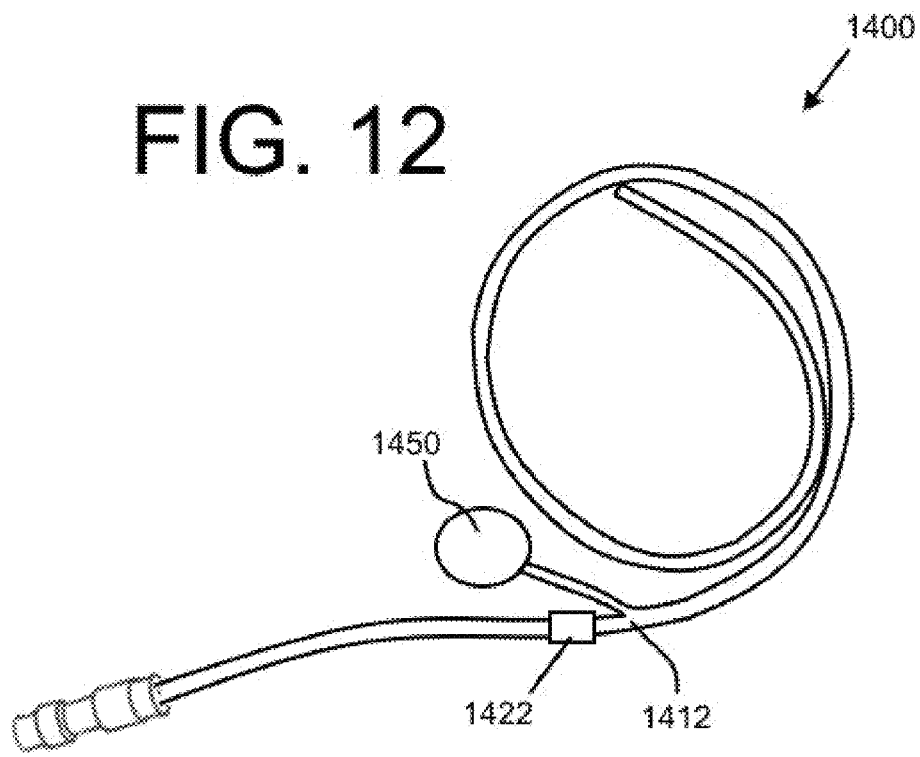
FIG. 12 shows an embodiment of a dual lumen indwelling catheter with a port in accordance with the present disclosure.

FIG. 12 shows an embodiment of a catheter 1400, which may be a dual lumen indwelling catheter similar to the catheter 200 of FIG. 2, but with a port 1450. The port 1450 may be a medical appliance that is deployed beneath the skin of a patient with a septum or other membrane through which can be injected. The septum may be located near the surface of the skin of the patient such that a needle can penetrate the skin and the septum to access a cavity of the port 1450. The cavity of the port 1450 may be in fluid communication with an injection lumen of the catheter 1400 such that the port 1450 provides an interface between a medical professional and the injection lumen of the catheter 1400. The injection lumen of the catheter 1400 may direct the injected medication or other substance from the port 1450 to a target location within the patient body as described in detail above. A cuff element 1422 may be included proximal to a junction 1412, as shown. It is also contemplated that the cuff element 1422 could be distal to the junction 1412. Embodiments with a port are described in more detail below.

Figure 13:
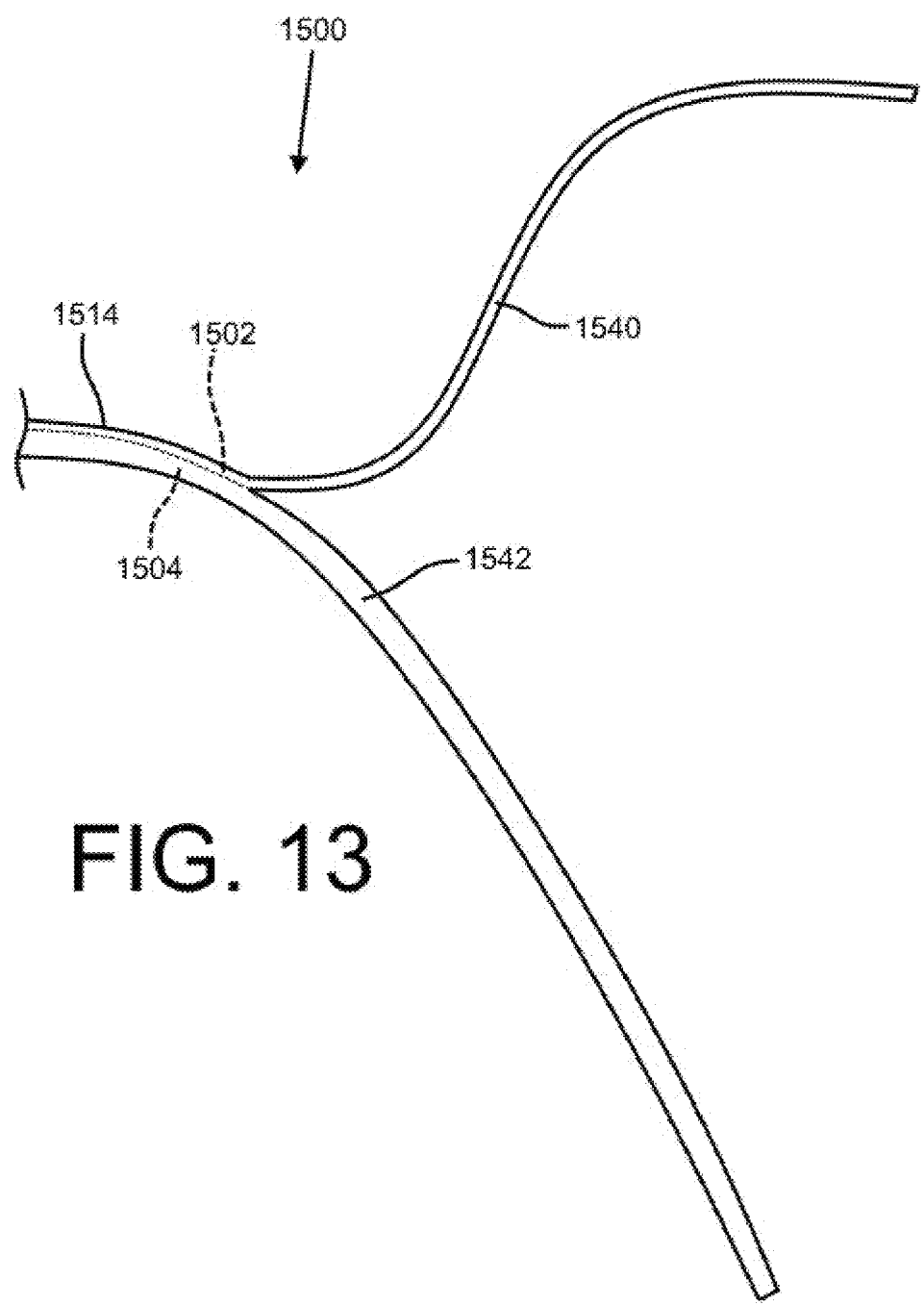
FIG. 13 shows a distal end of an embodiment of a catheter with bifurcated distal length having separated distal tube portions in accordance with the present disclosure.

FIG. 13 shows a distal end of a catheter 1500 with a bifurcated distal length having separated distal tube portions depicted as the first distal tube portion 1540 and the second distal tube portion 1542. The distal tube portions may be formed of a flexible silicone to provide patient comfort and in some embodiments may include a memory material for deployment to a specific area of a body cavity. The first distal tube portion 1540 and the second distal tube portion 1542 may extend from a binal portion 1514. A first lumen 1502, which may be an injection lumen, may extend through the binal portion 1514 and the first distal tube portion 1540. Similarly, the second lumen 1504, which may be a drainage lumen, may extend through the binal portion 1514 and the second distal tube portion 1542. The depicted bifurcated distal length of FIG. 13 may be combined with any of the embodiments disclosed herein.

Figure 14:
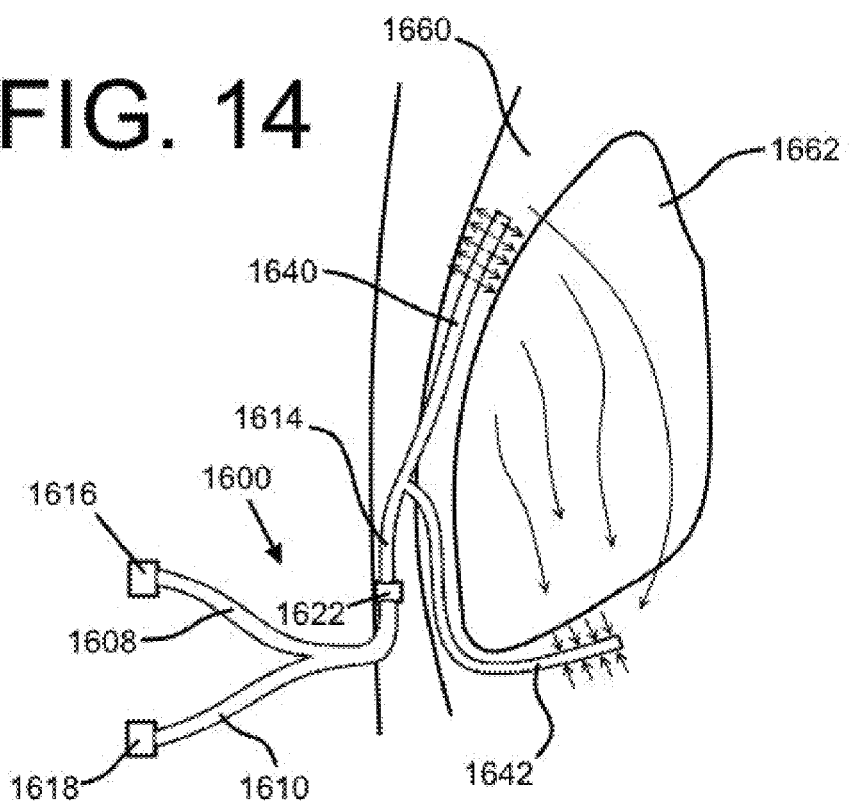
FIG. 14 shows an embodiment of a dual lumen indwelling catheter with a bifurcated distal length in accordance with the present disclosure.

For example, FIG. 14 shows a catheter 1600 having a bifurcated distal length with a first distal tube portion 1640 and a second distal tube portion 1642. The bifurcated distal length may be configured for deployment within a body cavity, such as the pleural space 1660 surrounding a lung 1662. The catheter 1600 also has a bifurcated proximal length with a first proximal tube portion 1608 and a second proximal tube portion 1610. The first proximal tube portion 1608 may include a first lumen, which may extend from the first proximal tube portion 1608, through a binal portion 1614, and to the first distal tube portion 1640. The first lumen may be an injection lumen similar to as described above, and the first distal tube portion 1640 may include a distal end with fenestrations for providing a particular distribution of an injected medication (e.g., the fenestrations of FIGS. 7-10 and/or the end features of FIG. 11). A first valve 1616 may provide access to the first lumen. The second lumen may be a drainage lumen similar to as described above, and the second distal tube portion 1642 may include fenestrations and/or other end features configured for drainage. A second valve 1618, which may be a different valve than the first valve 1616, may provide access to the second lumen. A cuff element 1622 may be included on the binal portion 1614 (or another portion) and may be configured for facilitating tissue ingrowth, as described above.

The embodiment of FIG. 14 may be advantageous for providing a lavage process of circulating a fluid through a body cavity. For example, a fluid medication or other fluid may be injected into an injection lumen at the first proximal tube portion 1608 through the first valve 1616. The fluid may the travel through the injection lumen of the catheter 1600 to a distal end of the first distal tube portion 1640, where it is injected into the depicted pleural space 1660. The first distal tube portion 1640 may be maneuvered in the pleural space during installation such that it is located at a relatively high location with respect to the second distal tube portion 1642. As such, the fluid may be pulled at least partially by the force of gravity through the pleural space 1660 to a respectively lower location (making contact with, and/or traveling through, the lung 1662, on its way). The second distal tube portion 1642 may be located at that relatively lower location to drain and remove the fluid from the pleural space 1660. It is contemplated that drainage lumen of the second distal tube portion 1642 may provide a suction force to facilitate the flow of the fluid. The fluid may then be pulled through the drainage lumen and exit the catheter 1600 at the second proximal tube portion 1610 through the second valve 1618. As described in more detail above (with reference to FIG. 2), the first and second valves may be different valve models configured for their particular function (e.g., drainage or injection).

Figure 15:
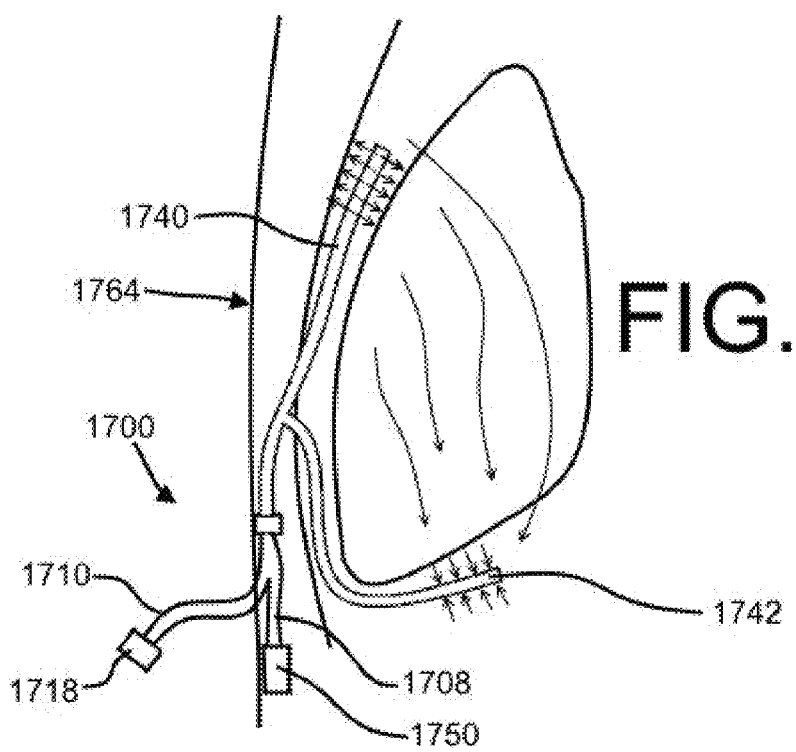
FIG. 15 shows an embodiment of a dual lumen indwelling catheter with a bifurcated distal length and including a port in accordance with the present disclosure.

FIG. 15 shows an embodiment of a catheter 1700 similar to the catheter 1600 of FIG. 14, but including a port 1750. The port 1750 may be located beneath the outer surface 1764 of the skin of a patient, and may provide an interface between a medical professional and a lumen (e.g., an injection lumen) of the catheter 1700. The port 1750 may be located on a first proximal tube portion 1708 associated with the injection lumen. A needle or other device (not shown) may be used to penetrate the skin and a septum of the port 1750 to inject a fluid into the port 1750, which may then flow to a distal end of the first distal tube portion 1740. The fluid may then move through the body cavity and be drained through the second distal tube portion 1742 and circulated back out of the catheter 1700 through the valve 1718.

This embodiment may be advantageous for concealing at least one of the proximal tube portions (in this case, the first proximal tube portion 1708). Further, it may ensure the first proximal tube portion 1708 is not confused with the second proximal tube portion 1710 and/or may ensure the injection lumen of the first proximal tube portion 1708 remains relatively inaccessible to the patient. The second proximal tube portion 1710 may remain accessible to the patient, and may be used in isolation by a medical professional, the patient, or another person to perform a drainage procedure separate from a lavage process. It is also contemplated that the port 1750 may be utilized during an injection procedure separate from a lavage process.

Another embodiment of a dual lumen catheter 1800 is shown in FIG. 16. The catheter 1800 may be similar to the catheters 1600, 1700 of FIGS. 14-15, but may include a circulating pump 1852. The circulating pump 1852 may receive a lavage fluid from a drainage lumen of the catheter 1800 and then circulate that fluid back to a body cavity through an injection lumen. This embodiment may be advantageous where it is desirable to circulate a medication through a particular area of a body cavity multiple times. Further, the fluid circulated through the catheter 1800 may be a suitable mixture of medication and body fluid or saline with a suitable concentration of the medication. It is contemplated that the circulating pump 1852 may be programmed to turn on and off automatically such that an appropriate number of lavage treatments are performed and such that each lavage treatment is performed for an appropriate amount of time. The circulation pump may optionally include filtration elements up to and including highly selective filters such as used in various dialysis machines, physically and/or chemically selective-binding elements, and/or other elements configured to remove, replace, and/or add in predetermined materials from/to the fluid and/or fluid-borne mixture. It is contemplated that the circulating pump 1852 may be controlled by the patient and/or the medical professional. In some embodiments, the circulating pump 1852 may be associated with a sensor that provides feedback to a pump controller.

Figure 17A:
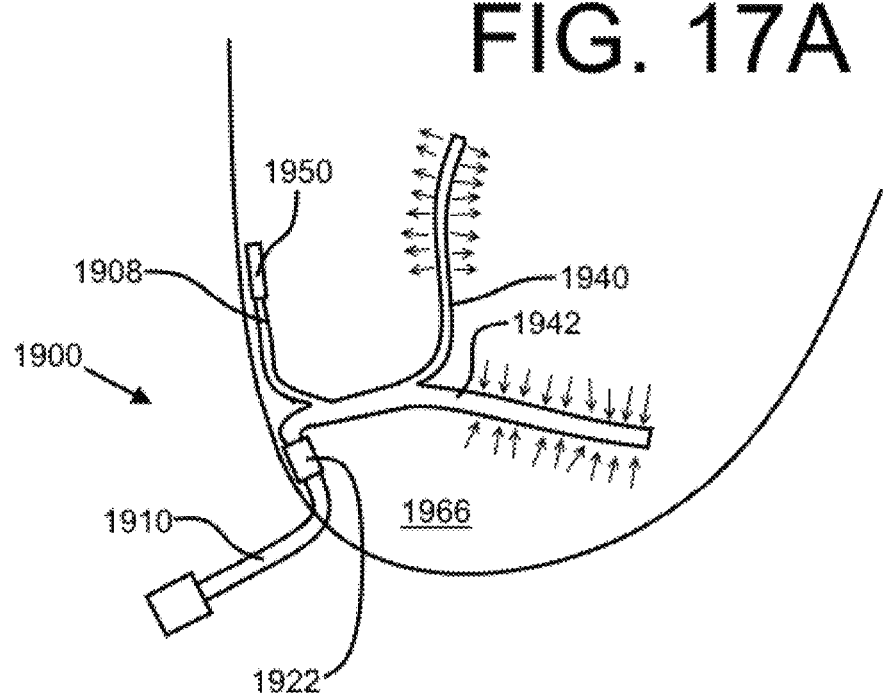
FIGS. 17A-B show two embodiments of a dual lumen indwelling catheter deployed in a peritoneal cavity and an organ, respectively, in accordance with the present disclosure.
Figure 17B:
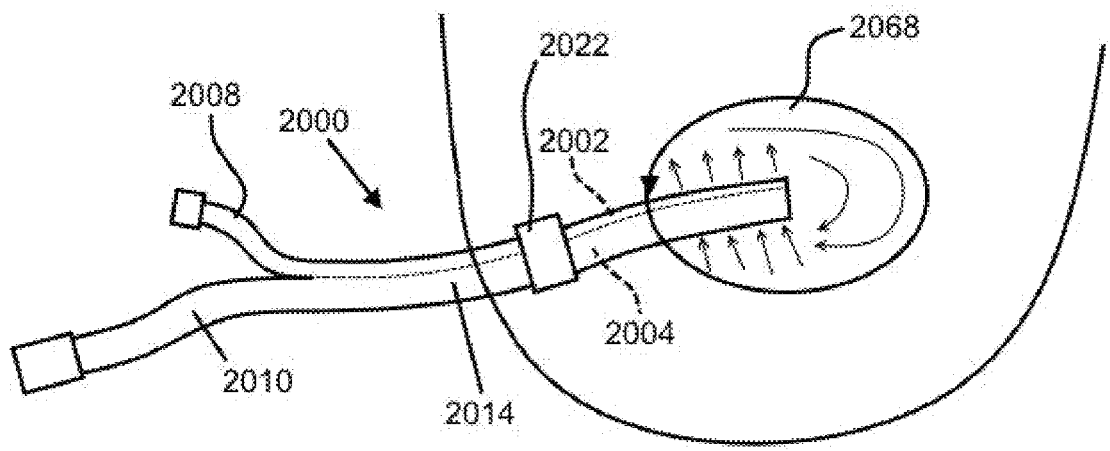

Herein, the embodiments of a dual lumen indwelling catheter are primarily described as intended for operation in the pleural cavity, but the present disclosure also covers catheters associated with other body cavities. Two non-limiting examples are shown in FIGS. 17A-17B. Referring to FIG. 17A, a catheter 1900 may be deployed in the peritoneal cavity 1966. Like many of the other embodiments described above, the catheter 1900 may include a first distal tube portion 1940 configured primarily for the injection of a fluid (e.g., a medication) and a second distal tube portion 1942 configured primarily for drainage. The catheter 1900 may include a first proximal tube portion 1908 with a port 1950 that remains under the skin of a patient and a second proximal tube portion 1910 that extends externally from the body of the patient when deployed. A cuff element 1922 may be located on the second proximal tube portion 1910, as shown.

Referring to FIG. 17B, a dual lumen catheter 2000 may be associated with an organ 2068 (e.g., a bladder). The catheter 2000 may have a bifurcated length with the first and second proximal tube portions 2008 and 2010 configured respectively for injection and drainage, for example, and respectively associated with an injection lumen 2002 and drainage lumen 2004. A binal portion 2014 may extend distally from the proximal tube portions to and beyond a sealing element 2022 and into the organ 2068. It is contemplated that a seal may be created where the binal portion 2014 enters the organ 2068. For example, when the organ 2068 is a urinary bladder, it may be necessary to provide a second and/or further plural sealing element(s) at the entry location of the bladder 2068 such that fluid from within the bladder does not leak to other areas of the patient body. The catheter 2000 is depicted without a bifurcated distal end, but this is not required. As shown, injected fluid may be circulated through the organ 2068 by injecting through the injection lumen 2002 and draining through the drainage lumen 2004 simultaneously (or seriatim, in this and other embodiments).

Figure 18:
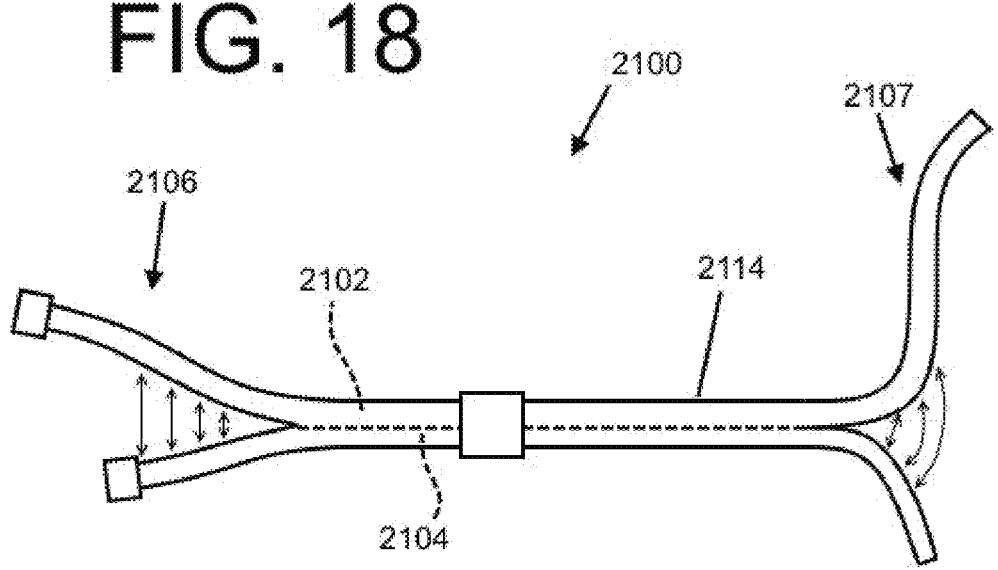
FIG. 18 shows an embodiment of a dual lumen indwelling catheter with separable tube portions and variable tube portion lengths in accordance with the present disclosure.

FIG. 18 shows an embodiment of a dual lumen indwelling catheter with separable or splittable tube portions. Referring to FIG. 18, the catheter 2100 may include a proximal bifurcated length 2106, a distal bifurcated length 2107, and a binal portion 2114 therebetween. The binal portion 2114 of the catheter 2100 may have a first lumen 2102 and a second lumen 2104 that are separable or splittable. For example, the first lumen 2102 and the second lumen 2104 may be connected via a relatively weak connection such that they can be pulled apart by a medical professional. When this occurs at the proximal end of the binal portion 2114, the length of the proximal bifurcated length 2106 may increase and the length of the binal portion 2114 may decrease. Similarly, when this occurs at the distal end, the bifurcated distal bifurcated length 2107 may increase and the length of the binal portion 2114 may decrease.

Advantageously, the catheter 2100 may therefore have dimensions that are adjustable to a particular medical procedure in a particular patient. For example, the catheter 2100 of FIG. 18 may be modified by a medical professional just before deployment rather than in a manufacturing facility.

Further, as depicted by FIG. 18, the bifurcated tube portions of the proximal bifurcated length 2106 may have different lengths (and, similarly, the lengths of the tube portions of the distal bifurcated length 2107 may be different). The lengths of these tube portions may be optimized for certain conditions and functions. For example, when a tube portion is associated with a port that may remain under the skin, it may be short with respect to a tube portion that will extend externally from a patient body. Similarly, a tube portion that must extend to a relatively remote location within a body cavity may be relatively long when compared to an internal tube portion. The length of the tube portions may be formed during the manufacturing of the catheter 2100. It is also contemplated that a medical professional may have the ability to cut one or more of the tube portions to an appropriate length before or during the deployment of the catheter 2100 (which may require attaching certain components, such as a valve and/or a port, after cutting the tube portions to length).

During an injection and/or drainage procedure, a variety of actions may be used to provide a desirable distribution of a drug. For example, it is contemplated that an internal portion of a catheter disclosed herein may be configured to vibrate or otherwise move during injection, and/or a device may be utilized to vibrate the patient's body (e.g., a vibrating chair). Additionally or alternatively, a pump connected to an injection lumen may provide a pulsing injection pressure, and/or a vacuum force associated with a drainage lumen may pulse. Injection may be continuous for a long period of time, or not. In some circumstances, it may be advantageous to use a single-use disposable pump designed to deliver (and/or drain) a precise amount of a medication or other fluid. A drug may be injected for minutes, hours, or days, followed by later drainage (or, alternatively, drainage can occur during or even before injection). Further, different drug types may be injected in a particular sequence. Injected drugs may be solid or liquid (including hydrogel) and may be heated or cooled. A sensor may be associated with the indwelling catheter to measure a parameter (such drug concentration in the body or in a drained fluid, for example), which may provide feedback to the patient, a medical professional, and/or an automatic system.

The embodiments disclosed herein may be advantageous for providing the ability to perform a variety of medical procedures. For example, a dual lumen indwelling catheter as described herein may provide the ability to inject a medication, such as a cancer-treating chemotherapy drug, into a body cavity and then remove that same medication before it can cause substantial damage to surrounding healthy tissue. This injection may be accomplished without surgery and it may be repeatable. Accordingly, the dose of medication may be optimized in view of the ability to repeat the procedure. It is also contemplated that the disclosed device could be utilized for other local treatments, such as localized antibiotic application, intentional introduction of chemical pleurodesis, immunotherapy or biologic therapy, or any other suitable procedure involving the introduction and/or the removal of fluid or other substances.

Those of skill in the art will appreciate that embodiments not expressly illustrated herein may be practiced within the scope of the present invention, including features described herein for different embodiments may be combined with each other and/or with currently-known or future-developed technologies while remaining within the scope of the claims presented here. For example, the various physical structures disclosed may also provide mechanical irritation promoting a desired sclerotic effect, and the structures and components disclosed herein may be combined with each other or other features. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. A catheter, the catheter comprising:
    a distal length formed as a single outer wall, multi-lumen tube extending to a distal end, the distal length configured to indwell a cavity of a patient body, the distal length comprising:
        a first lumen extending longitudinally through a lengthwise portion of the distal length, the first lumen at least partially defined by a first inner diameter surface of the distal length;
        a second lumen spaced from the first lumen extending longitudinally through the lengthwise portion of the distal length alongside the first lumen, the second lumen at least partially defined by a second inner diameter surface of the distal length and enclosed by a same outer perimeter of the single outer wall as the first lumen; and
        a first fenestration disposed through a side wall of the first lumen, the first fenestration configured to form an outlet of the first lumen; and
    a proximal length including a proximal lengthwise portion of the first lumen and a proximal lengthwise portion of the second lumen, wherein a cuff element is disposed on an outer surface of the proximal length;
    wherein a diameter of the second lumen is larger than a diameter of the first lumen, the first lumen connected to a first valve that is configured to connect to an injection system for injecting a medicament, the second lumen connected to a second valve that is configured to connect to a suction device for removing a fluid;
    wherein the same outer perimeter of the single outer wall encloses the first lumen and the second lumen, the single outer wall having a non-circular cross sectional shape with a relatively narrow portion comprising the first lumen and a relatively wide portion comprising the second lumen.

2. The catheter of claim 1,
    wherein the proximal length includes a bifurcated length having a first tube portion and a second tube portion,
    wherein the first lumen extends longitudinally through the tube first portion, and
    wherein the second lumen extends longitudinally through the second tube portion.

3. The catheter of claim 1, wherein a distal end of the distal length includes the first lumen with a plurality of fenestrations spaced longitudinally, wherein the space between the fenestrations decreases closer to a distal terminus.

4. The catheter of claim 1, wherein a distal end of the distal length includes the first lumen with a plurality of fenestrations spaced longitudinally, wherein a cross-sectional size of the fenestrations increases closer to a distal terminus.

5. The catheter of claim 1, wherein the diameter of the second lumen is at least two (2) times as large as the diameter of the first lumen.

6. The catheter of claim 1, wherein the proximal length includes a first proximal tube portion that includes an injection port.

7. A catheter, the catheter comprising:
    a first lumen and a second lumen;
    a binal portion formed as a single outer wall, multi-lumen tube, wherein a first inner diameter surface of the binal portion defines a side wall of at least a portion of the first lumen, wherein a second inner diameter surface of the binal portion defines a side wall of at least a portion of the second lumen such that the second lumen is spaced from and extends alongside the first lumen, wherein the first lumen and the second lumen are both enclosed by a same outer perimeter of the single outer wall, and wherein a distal length of the binal portion is configured to indwell a cavity of a patient body; and
    a bifurcated length located proximally of the binal portion, the bifurcated length including a first tube portion and a second tube portion, the first lumen extending longitudinally through the first tube portion, and the second lumen extending longitudinally through the second tube portion,
    wherein the first lumen is configured as an injection lumen, and wherein the second lumen is configured as a drainage lumen, a diameter of the second lumen is larger than a diameter of the first lumen, the first lumen connected to a first valve that is configured to connect to an injection system for injecting a medicament, the second lumen connected to a second valve that is configured to connect to a suction device for removing a fluid;
    wherein the binal portion has a non-circular cross sectional shape with a relatively narrow portion comprising the first lumen and a relatively wide portion comprising the second lumen.

8. The catheter of claim 7, further comprising a cuff element disposed on an outer surface of the binal portion.

9. The catheter of claim 7, wherein a distal end of the binal portion includes the first lumen with a plurality of fenestrations spaced longitudinally, wherein the space between the fenestrations decreases closer to a distal terminus.

10. The catheter of claim 7, wherein a distal end of the binal portion includes the first lumen with a plurality of fenestrations spaced longitudinally, wherein the space between the fenestrations decreases closer to a distal terminus.

11. The catheter of claim 7, wherein the diameter of the second lumen is at least two (2) times as large as the diameter of the first lumen.

12. A method of removing bodily fluid while delivering a medicament using a catheter for heated intraperitoneal chemoperfusion, the method comprising:
   performing a drainage procedure with a catheter having a distal length, the catheter comprising a binal portion at least partially formed as a single outer wall, multi-lumen tube including a first lumen and a second lumen that is spaced from and extends alongside the first lumen, the first lumen and the second lumen both being enclosed by a same outer perimeter of the single outer wall, the drainage procedure comprising:
      moving a bodily fluid within a cavity of a patient body from external the first lumen to internal the first lumen through a first fenestration; and
      moving the bodily fluid proximally within the first lumen to a proximal length of the catheter, wherein the proximal length of the catheter is located outside the patient body; and
   performing an injection procedure with the catheter, the injection procedure comprising:
      moving a medicament distally within the second lumen from the proximal length to a distal length, the distal length being located inside the patient body; and
      discharging the medicament from internal the second lumen to external the second lumen within the patient body;
   wherein a diameter of the second lumen is larger than a diameter of the first lumen, the first lumen connected to a first valve connected to an injection system, the second lumen connected to a second valve connected to a suction device;
   wherein the binal portion has a non-circular cross sectional shape with a relatively narrow portion comprising the first lumen and a relatively wide portion comprising the second lumen.

13. The method of claim 12, wherein the proximal length includes a cuff element disposed at a proximal end of the distal length on an outer surface of the catheter, the cuff element configured to provide a barrier between internal and external of the patient body.

14. The method of claim 12,
   wherein the proximal length includes a bifurcated length having a first tube portion and a second tube portion,
   wherein the first lumen extends longitudinally through the tube first portion, and
   wherein the second lumen extends longitudinally through the second tube portion.

15. The method of claim 12, the catheter including a bifurcated length located distally of the distal length and including a first distal tube portion and a second distal tube portion, wherein the first lumen extends longitudinally through the first distal tube portion, and wherein the second lumen extends longitudinally through the second distal tube portion.

* * * * *